United States Patent
Yu et al.

(10) Patent No.: US 11,028,039 B2
(45) Date of Patent: Jun. 8, 2021

(54) METHOD FOR PREPARING A β-HYDROXYCARBOXYLIC ACID ESTER

(71) Applicant: Shenyang Gold Jyouki Technology Co., Ltd, Liaoning (CN)

(72) Inventors: Kai Yu, Liaoning (CN); Wei Xu, Liaoning (CN)

(73) Assignee: Shenyang Gold Jyouki Technology Co., Ltd, Fushun (CN)

( * ) Notice: Subject to any disclaimer, the term of this patent is extended or adjusted under 35 U.S.C. 154(b) by 0 days.

(21) Appl. No.: 16/734,824

(22) Filed: Jan. 6, 2020

(65) Prior Publication Data
US 2020/0308093 A1 Oct. 1, 2020

(30) Foreign Application Priority Data
Mar. 26, 2019 (CN) .......................... 201910232918.1

(51) Int. Cl.
*C07C 67/37* (2006.01)
(52) U.S. Cl.
CPC .................................. *C07C 67/37* (2013.01)
(58) Field of Classification Search
CPC ..................................................... C07C 67/37
USPC .......................................................... 560/60
See application file for complete search history.

(56) References Cited

FOREIGN PATENT DOCUMENTS

JP 2004231542 A * 4/2004

OTHER PUBLICATIONS

Hamasaki et al. Tetrahedron Letters 52 (2011) 6869-6872.*
Cahiez et al. Chem. Rev. 2010, 110, 1435-1462.*
Machien translation of JP2004231542, 2004.*

* cited by examiner

*Primary Examiner* — Ana Z Muresan
(74) *Attorney, Agent, or Firm* — Enshan Hong; VLP Law Group LLP

(57) ABSTRACT

A method of preparing β-hydroxycarboxylic acid ester comprises mixing an alkylene oxide, a monohydric alcohol and a composite catalyst, and performing a carbonylation esterification reaction in a carbon monoxide atmosphere to obtain the β-hydroxycarboxylic acid ester. The composite catalyst comprises a main catalyst, a cocatalyst and a reducing agent. the main catalyst is at least one of a cobalt salt, cobalt oxide and cobalt hydroxide. The cocatalyst is a nitrogen-containing heterocyclic compound. The reducing agent is a base metal. The method is an atomic reaction type process, does not produce three wastes, and has high conversion rate. It is a green environmental protection process. The composite catalyst used does not contain $Co_2(CO)_8$. The raw materials and catalyst used are all cheap and easily available. The composite catalyst can be used repeatedly at a lower cost, and is suitable for industrial applications.

6 Claims, 5 Drawing Sheets

METHOD FOR PREPARING A β-HYDROXYCARBOXYLIC ACID ESTER

CROSS-REFERENCES TO RELATED APPLICATIONS

This application claims priority from Chinese Patent Application No. 201910232918.1 filed Mar. 26, 2019, the entire content of which is incorporated herein as reference.

BACKGROUND OF THE APPLICATION

1. Technical Field

The present application relates to the technical field of organic synthesis, in particular to a preparation method of a β-hydroxycarboxylic acid ester.

2. Background Art

β-Hydroxycarboxylates (3-hydroxycarboxylates) are a class of stable and important bifunctional platform compounds, widely used in pharmaceuticals, dietary supplements, pesticides, cosmetics, food additives, polyesters and other important industries, and synthesis of chiral fine compounds.

There are many methods for synthesizing mixed β-hydroxycarboxylates, mainly chemical synthesis, reduction hydrogenation, alkylene oxide carbonylation and carbonylation esterification. Hlavinka et al. (One-step deprotonation route to zinc amide and ester enolates for use in aldol reaction and Negishi couplings; Tetrahedron Letters, vol. 47, 29, 2006; P5049-5053) used a chemical synthesis method to condense aldehydes and ethyl acetate with bis(2,2,6,6-tetramethyl-1-piperidine)zinc as a catalyst, obtained the target product, but the yield was only 42%, the separation was very difficult; Showa Denko K.K. (EP1591531) used sodium borohydride method to get target product, but the reaction yield was only 74%, the raw material cost was high. In the preparation of β-hydroxycarboxylates by alkylene oxide carbonylation and esterification, cobalt carbonylation is usually required, and the synthesis conditions are harsh, and the yield is low. For example, Eisenmann et al. reported that $Co_2(CO)_8$ is a catalyst for the synthesis of 3 hydroxybutyric acid. The reaction of methyl ester requires 130° C., the pressure of CO needs to reach 24 MPa, but the reaction yield is only 40%, due to high temperature and high pressure, more by-products (J. L. Eisenmann, R. L. Yamartino, J. F. Preparation of Methy 1 β-hydroxybutyrate from Propylene Oxide, Carbon Monoxide, Methanol, and Dicobalt Octacarbony, J. Org. Chen., 1961, 26, 2102-2104).

At present, chiral β-hydroxycarboxylic acid esters are mainly produced by chemical synthesis, asymmetric catalytic hydrogenation and enzymatic methods. Among them, the chemical synthesis method uses chiral epichlorohydrin as a raw material, and after cyanide open-loop, nitrile hydrolysis and esterification, there are defects such as the use of highly toxic sodium cyanide, long route, cumbersome operation, and large amount of waste (such as prior art US20060264652); Asymmetric catalytic hydrogenation adopts a relatively expensive chiral phosphorus ligand catalyst, requires special acid-resistant high-pressure reaction equipment, the catalyst cannot be applied, greatly increases the production cost (such as prior art WO2005049545); The enzymatic method requires high purity of the substrate. The hydrogenation enzyme used needs to be obtained by multiple derivatization techniques, and expensive coenzyme needs to be added during the reaction process. The treatment process is cumbersome, the equipment output is relatively low, and the equipment occupancy rate is high (such as prior art CN200910183017.4). At present, although the raw materials used in the asymmetric catalytic hydrogenation method and the enzymatic method have a certain production amount, the process conditions are harsh or complicated, and diketene, an odorous and toxic flammable liquid, is used in the preparation process, and the production process is more dangerous. Jacobsen et al. (Regioselective carbomethoxylation of chiral epoxides: a new route to enantiomerically pure β-hydroxy ester; J. Org. Chem., 1999, 64(7), 2164-2165) used a $Co_2(CO)_8$ and 3-hydroxypyridine catalytic system to achieve the carbonylation of chiral epoxy compounds under relatively mild conditions. Chen Jing et al. (CN103420837A) used $Co_2(CO)_8$, $ZnBr_2$ and pyridine systems to obtain a chiral β-hydroxy ester by a simple process; however, they all used expensive $Co_2(CO)_8$ (metal glycosyl compounds, a complex), and the catalyst is very harsh in storage and use conditions, and industrialization cannot be achieved.

Based on the foregoing, neither the synthesis method of the mixed β-hydroxycarboxylic acid ester nor the synthesis method of the chiral β-hydroxycarboxylic acid ester can achieve industrial production.

SUMMARY OF THE APPLICATION

The present application provides a method for preparing a β-hydroxycarboxylic acid ester. The method in accordance with the present application involves a type of atomic reaction. No three wastes are produced. The process is simple and easy to implement, and the raw material is cheap and easy to obtain and is suitable for industrial production.

The present application provides a preparation method of a β-hydroxycarboxylic acid ester, comprising the following steps: mixing an alkylene oxide, a monohydric alcohol and a composite catalyst, and performing a carbonylation esterification reaction in a carbon monoxide atmosphere to obtain the β-hydroxycarboxylic acid ester.

The composite catalyst comprises a main catalyst, a cocatalyst and a reducing agent. The main catalyst is a cobalt salt, cobalt oxide or cobalt hydroxide. The cocatalyst is a nitrogen-containing heterocyclic compound. The reducing agent is a base metal.

Preferably, the ratio of the molar amount of the main catalyst, the cocatalyst and the reducing agent is (1:2) to (6:2) to (10).

Preferably, the amount of the main catalyst is from 0.5 to 5 mol % based on the alkylene oxide.

Preferably, the cobalt salt comprises at least one of cobalt fluoride, cobalt chloride, cobalt bromide, cobalt iodide, cobalt acetate, cobalt carbonate, cobalt nitrate, and cobalt sulfate.

Preferably, the nitrogen-containing heterocyclic compound includes at least one of a pyrazole compound, an imidazole compound, a pyridine compound, and a quinoline compound.

Preferably, the pyrazole compound comprises at least one of pyrazole, 1-methylpyrazole, and 2-methylpyrazole; and the imidazole compound comprises at least one of imidazole, 1-methylimidazole, 4-phenylimidazole, and 1-acetyl. The pyridine compound comprises at least one of pyridine, 3-hydroxypyridine, 2-hydroxypyridine, 2-aminopyridine, 4-aminopyridine, 4-N,N-lutidine, 2,2-bipyridine, and 4,4-bipyridine. The quinoline compound comprises at least one of quinoline, isoquinoline, and 8-hydroxyquinoline.

Preferably, the base metal comprises at least one of iron, zinc, manganese, nickel, copper, and aluminum.

Preferably, the ratio of the propylene oxide to the monohydric alcohol is 1 mmol: 1 to 5 mL.

Preferably, the carbonylation esterification reaction is carried out at a pressure of 3 to 10 MPa, a temperature of 40 to 120° C., and a time of 10 to 30 hours.

The present application provides a method for preparing a β-hydroxycarboxylic acid ester, comprising the steps of: mixing an alkylene oxide, a monohydric alcohol and a composite catalyst, and performing a carbonylation esterification reaction in a carbon monoxide atmosphere to obtain a β-hydroxycarboxylic acid ester. The composite catalyst comprises a main catalyst, a cocatalyst and a reducing agent. The cocatalyst is at least one of a cobalt salt, cobalt oxide and cobalt hydroxide. The cocatalyst is a nitrogen-containing heterocyclic compound. The reductive agent is a base metal. This application uses the alkylene oxide, the monohydric alcohol, and the carbon monoxide as raw materials to directly obtain the β-hydroxycarboxylic acid ester by a one-step method, is an atomic reaction type process, does not generate three wastes, has high conversion rate, is a green environmental protection process at the same time. The composite catalyst used does not contain $Co_2(CO)_8$. The raw materials and catalyst are cheap and easy-to-obtain materials. The composite catalyst can be repeatedly applied, and the cost is low, which is suitable for industrial applications. Further, when the present application is used for the preparation of a chiral β-hydroxycarboxylic acid ester, the obtained chiral-hydroxycarboxylic acid ester does not undergo racemization and does not lower the optical activity of the substrate.

DETAILED DESCRIPTION OF PREFERRED EMBODIMENTS OF THE APPLICATION

Figure 1:
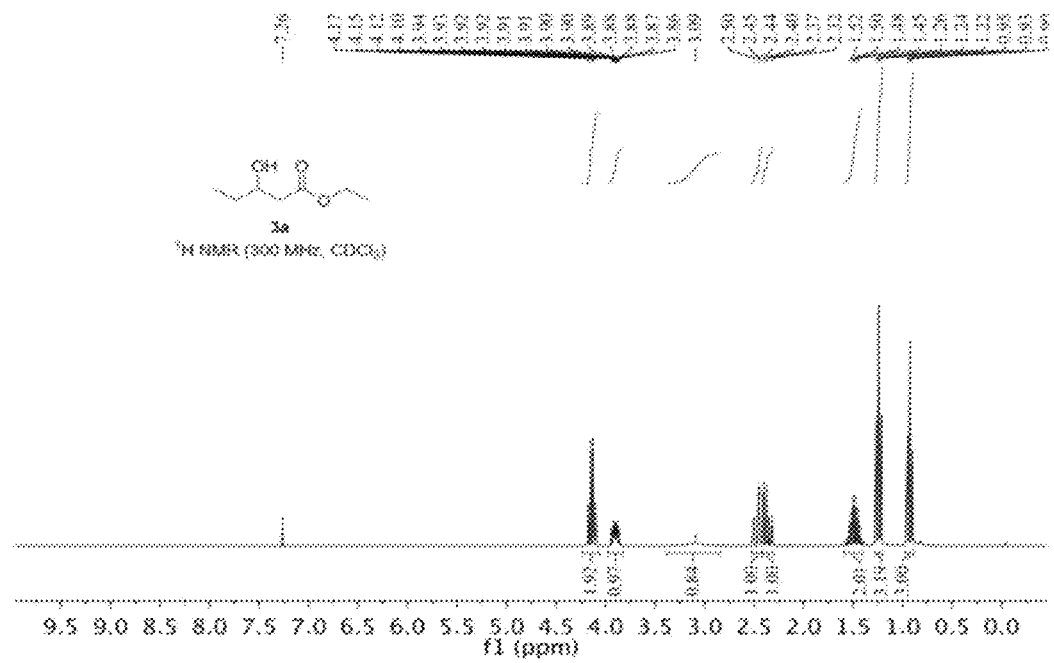
FIG. 1 is the hydrogen spectrum of the product obtained in Example 1.

To help those skilled in the art to understand the present application, the present application will be further detailed below in combination with examples and accompanying drawings. Contents mentioned in the examples are not intended to limit the present application.

The present application provides a preparation method of a β-hydroxycarboxylic acid ester, comprising the following steps: mixing an alkylene oxide, a monohydric alcohol and a composite catalyst, and performing a carbonylation esterification reaction in a carbon monoxide atmosphere to obtain a β-hydroxycarboxylic acid ester.

The composite catalyst comprises a main catalyst, a cocatalyst and a reducing agent; the main catalyst is a cobalt salt, cobalt oxide or cobalt hydroxide; the cocatalyst is a nitrogen-containing heterocyclic compound; and the reducing agent is a base metal.

The type of the propylene oxide in this application is not particularly limited, and those technical staff can select a suitable propylene oxide depending on the structure of the target product. In the embodiment of the present application, the propylene oxide is preferably any one of the compounds represented by formulas I to V:

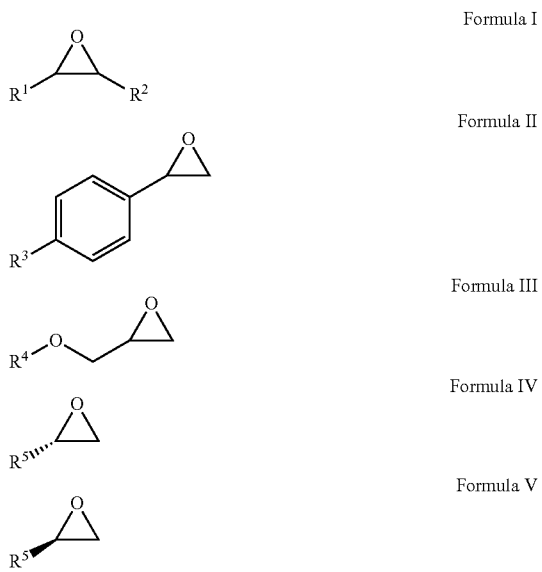

Wherein $R^1$ is preferably H, $CH_3$, $CH_2Cl$, $CH_2Br$, $CH_2OH$, $CH_2(CH_2)_mCH_3$ or $CH_2(CH_2)_nH=CH_2$, m=0~12, n=0~12; $R^2$ is preferably H, $CH_3$, $CH_2Cl$, $CH_2Br$, $CH_2OH$, $CH_2(CH_2)_pCH_3$ or $CH_2(CH_2)_qH=CH_2$, p=0~12, q=0~12; $R^3$ is preferably H, $CH_3$, Cl, Br or $OCH_3$; $R^4$ is preferably $CH_3$, $C(CH_3)_3$ or Ph; $R^5$ is preferably $CH_3$, $C(CH_3)_3$, $CH_2Cl$, $CH_2Br$, $CH_2OH$, Ph, $CH_2OPh$, $CH_2OCH_3$, $CH_2OC(CH_3)_3$, $(CH_2)_fH=CH_2$, e=0~12, f=0~12.

The specific kind of the monohydric alcohol in our application is not particularly limited, and those skilled in the art can select a suitable monohydric alcohol according to the target product. In an embodiment of the application, the monohydric alcohol is preferably methanol, ethanol, propanol, butanol, isopropanol, benzyl alcohol or phenylethyl alcohol.

In the present application, the ratio of the molar amounts of the main catalyst, the cocatalyst and the reducing agent is preferably 1:(2 to 6):(2 to 10); more preferably 1:(3 to 5): (4 to 6).

In the present application, the amount of the main catalyst is preferably from 0.5 to 5 mol % based on the alkylene oxide, more preferably from 1 to 3 mol %.

In the present application, the cobalt salt preferably includes cobalt fluoride, cobalt chloride, cobalt bromide, cobalt iodide, cobalt acetate, cobalt carbonate, cobalt nitrate, or cobalt sulfate.

In the present application, the nitrogen-containing heterocyclic compound preferably comprises at least one of a pyrazole compound, an imidazole compound, a pyridine compound, and a quinoline compound.

In the present application, the pyrazole compound preferably comprises at least one of pyrazole, 1-methylpyrazole, and 2-methylpyrazole; and the imidazole compound preferably comprises at least one of imidazole, 1-methylimidazole, 4-phenylimidazole, and 1-acetylimidazole; the pyridine compound preferably comprises at least one of pyridine, 3-hydroxypyridine, 2-hydroxypyridine, 2-aminopyridine, 4-aminopyridine, 4-N,N-dimethylpyridine, 2,2-bipyridine, and 4,4-bipyridine; the quinoline compound preferably comprises at least one of quinoline, isoquinoline, and 8-hydroxyquinoline.

In the present application, the base metal preferably includes at least one of iron, zinc, manganese, nickel, copper, and aluminum.

In the present application, the ratio of the propylene oxide to the monohydric alcohol is preferably 1 mmol: 1 to 5 mL.

The mixing sequence of the alkylene oxide, the monohydric alcohol and the composite catalyst in our application is not particularly limited. In the embodiment of the present application, the main catalyst and the reducing agent are preferably added to the reaction vessel, and then the cocatalyst, the alkylene oxide and the monohydric alcohol are added under a protective atmosphere; the protective atmosphere is preferably nitrogen or an inert gas. In the present application, the protective atmosphere is capable of removing oxygen in the container.

The method for creating the carbon monoxide atmosphere of this application is not particularly limited, and a conventional method for creating a gas atmosphere can be used. In the embodiment of the present application, after obtaining the mixture of the alkylene oxide, the monohydric alcohol and the composite catalyst in the protective atmosphere, the protective gas in the reaction vessel is replaced with carbon monoxide gas for 3 to 5 times, and then charge the carbon monoxide gas to the pressure required for the carbonylation esterification reaction.

In the present application, the pressure of the carbonylation esterification reaction is preferably 3 to 10 MPa, the temperature is preferably 40 to 120° C., and the time is preferably 10 to 30 hours; and the time is preferably counted from the time required to reach the temperature required for the carbonylation esterification reaction. In the present application, the pressure and temperature of the carbonylation esterification reaction are mild, and the requirements for the reaction equipment are low.

After completion of the carbonylation esterification reaction, the present application preferably releases the pressure, and the obtained reaction liquid is subjected to distillation, and the middle stage fraction is taken to obtain a β-hydroxycarboxylic acid ester. The reaction solution obtained by the preparation method provided by the application can be subjected to simple distillation to obtain a β-hydroxycarboxylic acid ester of higher purity.

The specific mode of the distillation of the present application is not particularly limited, and those skilled in the art can determine the conditions of distillation according to the boiling point of the monohydric alcohol used, that is, determine the product by vacuum distillation or rectification. During the distillation process, the monohydric alcohol has the lowest boiling point, as the first fraction is first distilled off, and the high-boiling impurities are rare; a small amount of the product and the catalyst remain at the bottom of the kettle and are used directly next time.

In the present application, the catalyst can be recycled, and specific catalysts can be appropriately added according to different reaction substrates to ensure that the reaction activity and product quality are not affected. The preparation method of a 3-hydroxycarboxylic acid ester provided by the present application will be described in detail below with reference to the examples, but they are not to be construed as limiting the scope of the present application.

Example 1

The reaction equation of this embodiment is as shown in the following scheme (1):

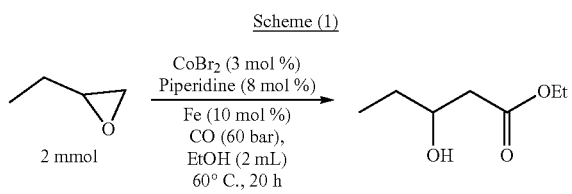

The specific steps are as follows: 13.11 mg of $CoBr_2$ and 11.17 mg of iron powder are mixed and placed in a reactor; the reactor is filled with nitrogen and vacuumed, and thus repeated three times to obtain a nitrogen atmosphere, and 2 mL of ethanol is added to the reactor. 144.22 mg (2 mmol) of 1,2-butylene oxide and 13.62 mg of piperidine, then replacing the nitrogen in the reactor with carbon monoxide gas, replacing it three times, charging carbon monoxide to 6 MPa, raising the temperature to 60° C., and reacting for 20 hours; After completion, the obtained reaction liquid is subjected to distillation to obtain 269 mg of a product having a content of 99% and a yield of 92%.

Figure 2:
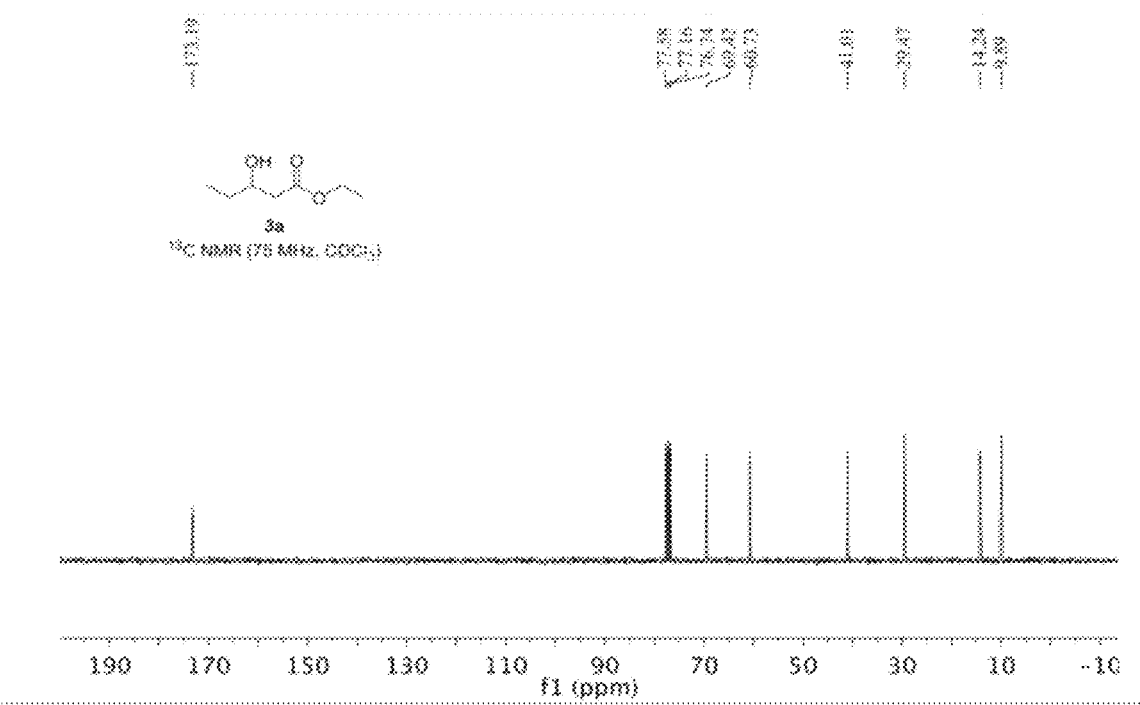
FIG. 2 is the carbon spectrum of the product obtained in Example 1.

Under the protection of nitrogen, the iron powder is added to the residue, and 2 ml of ethanol and 144.22 mg (2 mmol) of 1,2-butylene oxide are added, and the above-mentioned synthesis operation is repeated, and the product content and the yield are unchanged;

The product obtained in this example is subjected to nuclear magnetic characterization, and the analysis-diagram are shown in FIG. 1 and FIG. 2, and the specific results are as follows:

$^1$H NMR (300 MHz, $CDCl_3$) δ 4.14 (q, J=7.1 Hz, 2H), 3.97-3.82 (m, 1H), 3.09 (s, 1H), 2.48 (dd, J=16.3, 3.4 Hz, 1H), 2.36 (dd, J=16.3, 8.9 Hz, 1H), 1.59-1.39 (m, 2H), 1.24 (t, J=7.1 Hz, 3H), 0.93 (t, J=7.4 Hz, 3H).

$^{13}$C NMR (75 MHz, $CDCl_3$) δ 173.19, 69.42, 60.73, 41.01, 29.47, 14.24, 9.89.

The product obtained in this example is analyzed by gas chromatography-mass spectrometry and the results are as follows:

GC-MS (EI, 70 eV): m/z (%)=145(5), 128(10), 117(100), 101(25), 89(40), 71(70).

According to the above analysis, it is understood that the product obtained in the present application is ethyl 3-hydroxyvalerate having a structure of the product represented by the Scheme (1).

Example 2

Under a nitrogen atmosphere, 5.60 mg of iron powder was added to the residue of Example 1, and then 2 mL of ethanol and 144.22 mg (2 mmol) of 1,2-butylene oxide were added, and the subsequent steps were carried out in accordance with the method of Example 1. Finally, 270.7 mg of product was obtained with a content of 99% and a yield of 92.6%. The obtained product was subjected to the same nuclear magnetic resonance test results as in Example 1.

Example 3

The reaction equation of this embodiment is represented by the following Scheme (2):

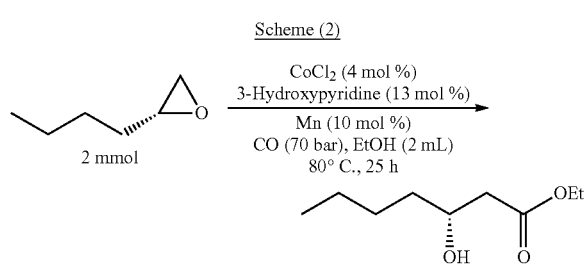

Scheme (2)

The specific steps are as follows: 10.37 mg of CoCl$_2$ and 10.97 mg of manganese powder are placed in the reactor; the reactor is filled with nitrogen and vacuumed, and thus repeated three times to obtain a nitrogen atmosphere, and 2 mL of ethanol and 200 mg are added to the reactor. (2 mmol) R-1,2-epoxyhexane (e.e. value: 99.59%) and 24.69 mg of 3-hydroxypyridine, and then replacing the nitrogen in the reactor with carbon monoxide gas, replacing it three times, and then charging carbon monoxide to 7 MPa. The temperature is raised to 80° C., and the reaction is carried out for 25 hours. After the completion of the reaction, the obtained reaction liquid is subjected to distillation under reduced pressure to give 314 mg of a colorless transparent liquid having a content of 99%, and a yield of 90%.

Figure 3:
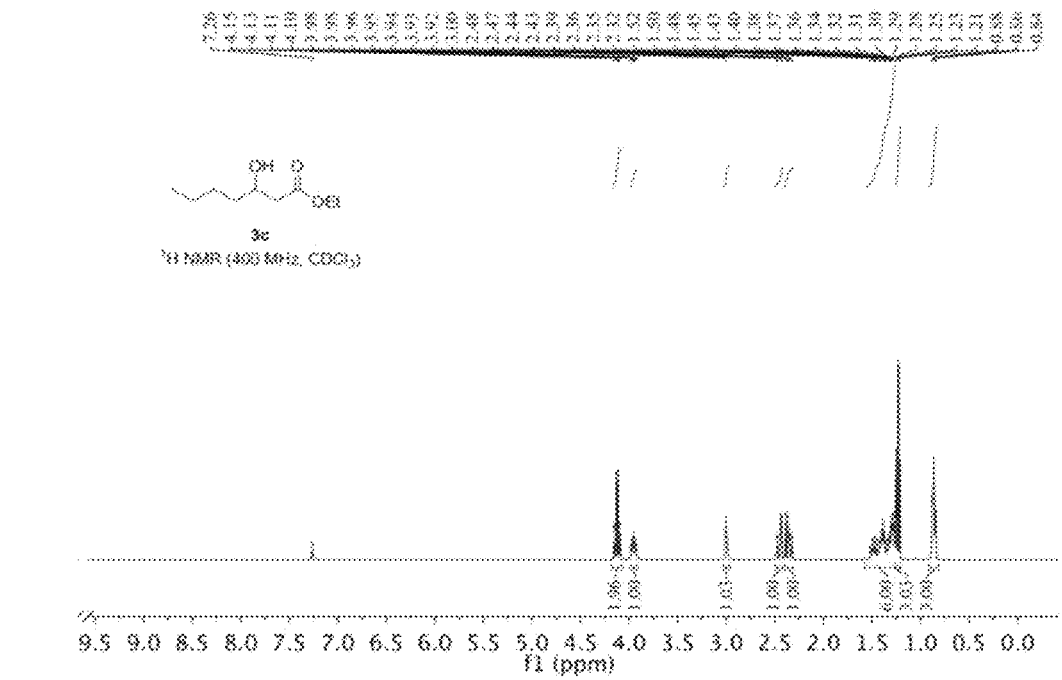
FIG. 3 is the hydrogen spectrum of the product obtained in Example 2.
Figure 4:
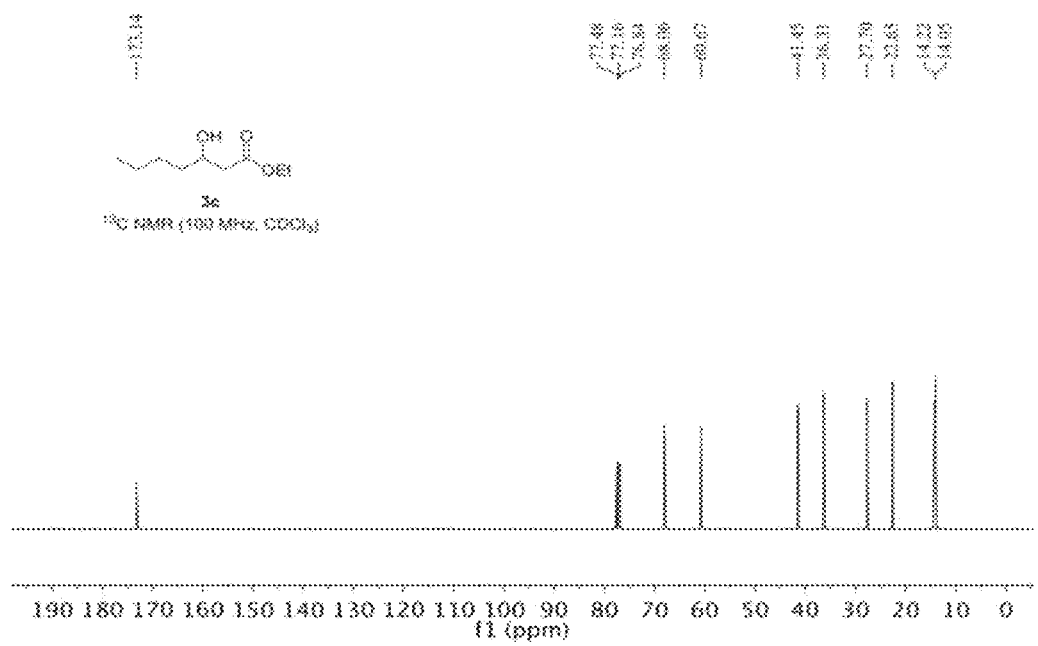
FIG. 4 is the carbon spectrum of the product obtained in Example 2.

The product obtained in this example is characterized by NMR, and the analysis-diagram are shown in FIGS. 3 and 4, and the results are as follows:

$^1$H NMR (400 MHz, CDCl$_3$) δ 4.12 (q, J=7.1 Hz, 2H), 3.99-3.92 (m, 1H), 3.00 (s, 1H), 2.45 (dd, J=16.3, 3.3 Hz, 1H), 2.35 (dd, J=16.3, 8.9 Hz, 1H), 1.56-1.26 (m, 6H), 1.23 (t, J=7.1 Hz, 3H), 0.86 (t, J=7.1 Hz, 3H).

$^{13}$C NMR (101 MHz, CDCl$_3$) δ 173.14, 68.06, 60.67, 41.45, 36.31, 27.70, 22.65, 14.22, 14.05.

The product obtained in this example is analyzed by gas chromatography-mass spectrometry and the results are as follows:

GC-MS (EI, 70 eV): m/z (%)=174(1), 156(5), 127(10), 117(100), 88(35), 71(55).

According to the above analysis, it is understood that the product obtained in the present application is R-3-hydroxyheptanoic acid ethyl ester having the structure of the product represented by the Scheme (2).

Figure 5:
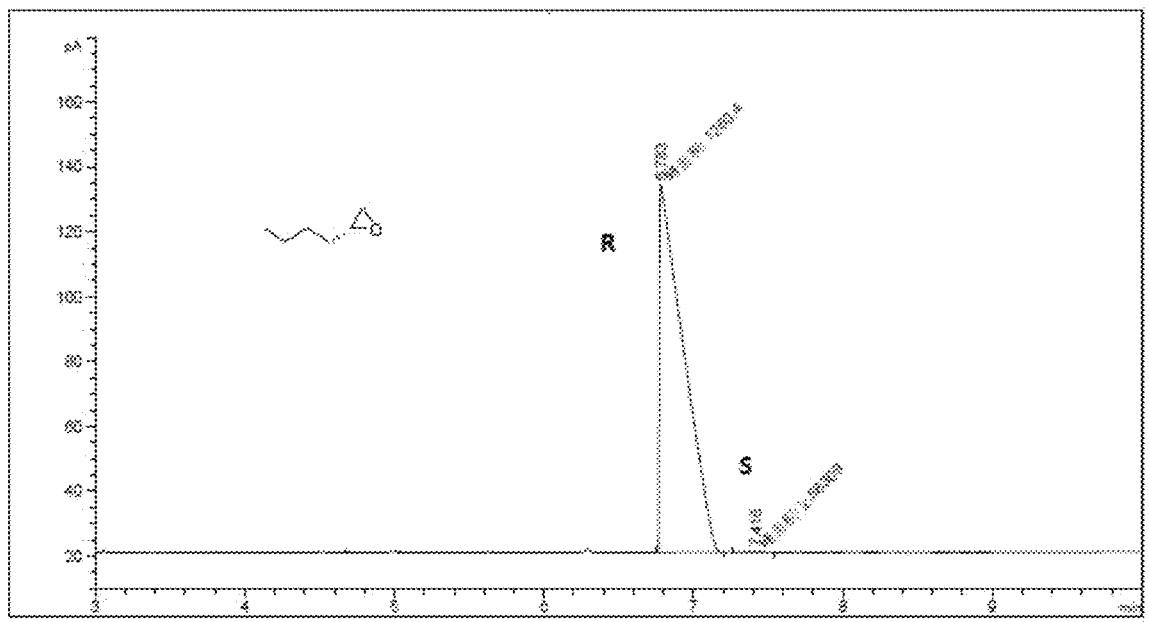
FIG. 5 is the graph showing the results of optical purity test of the raw materials used in Example 2.
Figure 6:
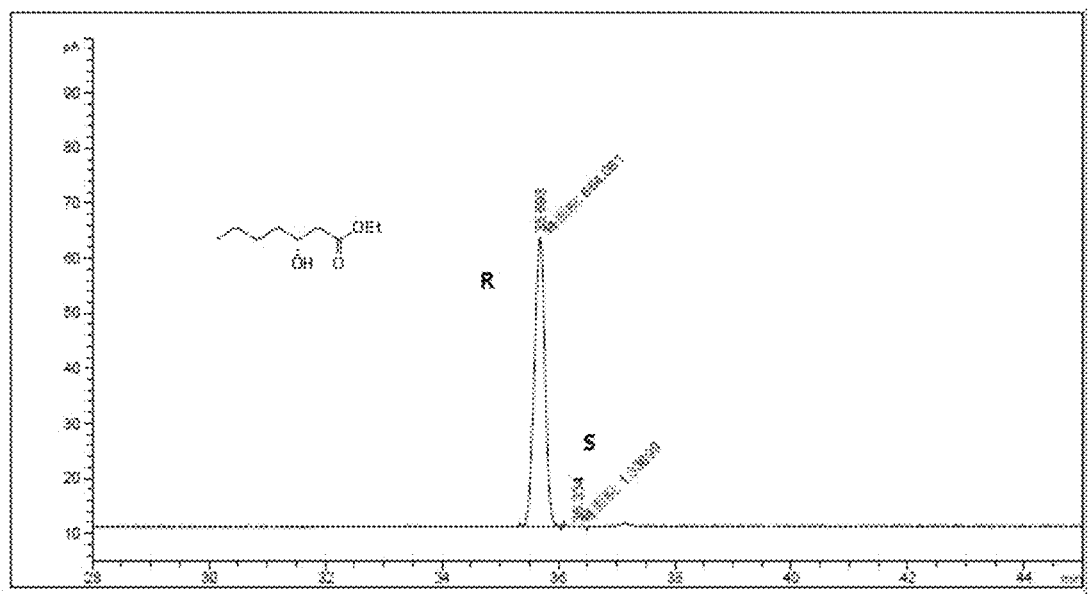
FIG. 6 is the graph showing the results of optical purity test of the product obtained in Example 2.

The optical purity of the raw material is measured. As shown in FIG. 5, the e.e. value is 99.59%. The optical purity of the product obtained in the present example is measured. As shown in FIG. 6, the e.e. value is 99.59%, and the e.e. value do not substantially change, it is indicated that the preparation method of the present application does not undergo racemization.

Example 4

The reaction equation of this embodiment is as shown in the following Scheme (3):

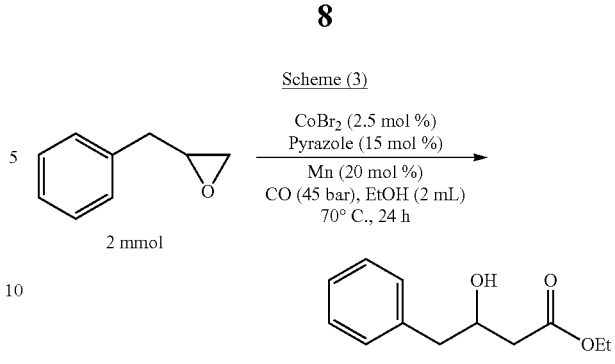

Scheme (3)

The specific steps are as follows: 10.92 mg of CoBr$_2$ and 21.95 mg of manganese powder are placed in the reactor; the reactor is filled with nitrogen and vacuumed, and thus repeated three times to obtain a nitrogen atmosphere, and 2 mL of ethanol is added to the reactor, and 268 mg (2 mmol) of (2,3-epoxypropyl)benzene and 20.40 mg of pyrazole, then replacing the nitrogen in the reactor with carbon monoxide gas, replacing it three times, then charging carbon monoxide to 4.5 MPa, and raising the temperature to 70° C., and reacting for 25 hours. After completion of the reaction, the obtained reaction mixture is subjected to distillation under reduced pressure to give 378.5 mg of a colorless transparent liquid, having a content of 99% and a yield of 91%.

Figure 7:
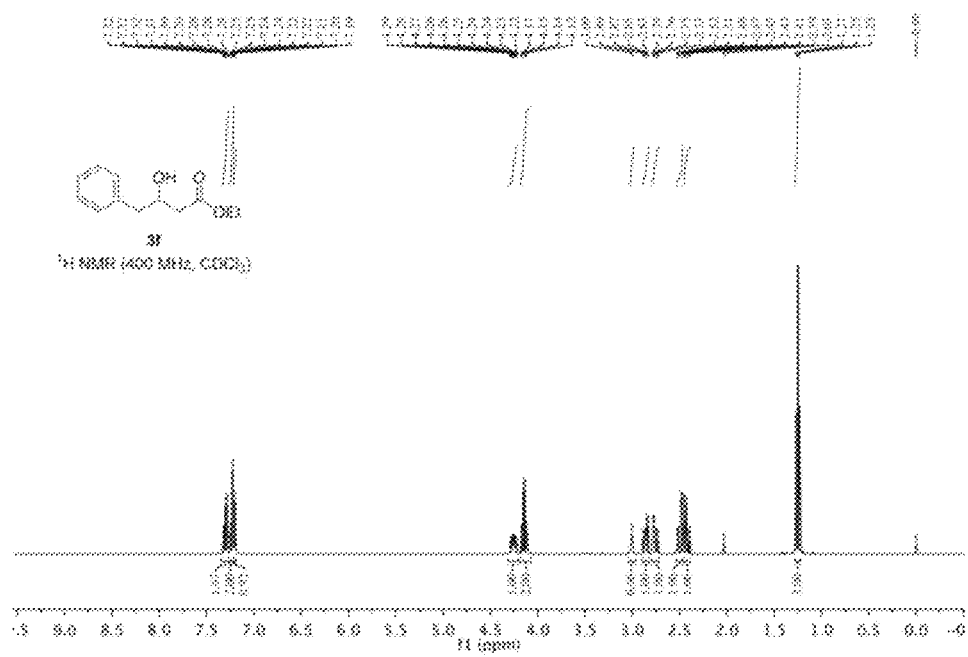
FIG. 7 is the hydrogen spectrum of the product obtained in Example 3.
Figure 8:
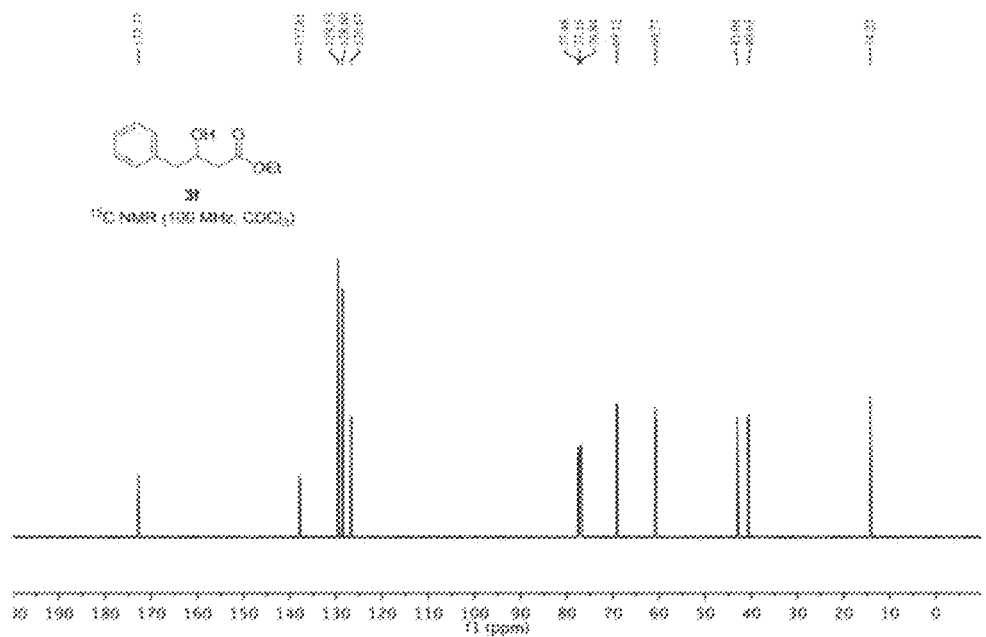
FIG. 8 is the carbon spectrum of the product obtained in Example 3.

The products obtained in this example are characterized by NMR, and the analytical maps are shown in FIGS. 7 and 8. The results are as follows:

$^1$H NMR (400 MHz, CDCl$_3$) δ 7.33-7.27 (m, 2H), 7.25-7.21 (m, 2H), 7.21-7.19 (m, 1H), 4.31-4.21 (m, 1H), 4.14 (q, J=7.2 Hz, 2H), 3.00 (s, 1H), 2.86 (dd, J=13.6, 7.1 Hz, 1H), 2.76 (dd, J=13.6, 6.2 Hz, 1H), 2.50 (dd, J=16.4, 3.7 Hz, 1H), 2.42 (dd, J=16.4, 8.6 Hz, 1H), 1.25 (t, J=7.1 Hz, 3H).

$^{13}$C NMR (101 MHz, CDCl$_3$) δ 172.77, 137.81, 129.53, 128.60, 126.67, 69.12, 60.77, 43.04, 40.63, 14.23.

The product obtained in this example is analyzed by gas chromatography-mass spectrometry and the results are as follows:

GC-MS (EI, 70 eV): m/z (%)=190(32), 145(20), 117 (100), 91(74), 71(30).

According to the above analysis, the product obtained in the present application is ethyl 3-hydroxy-4-phenylbutanoate having a structure of the product represented by the Scheme (3).

Example 5

The reaction equation of this embodiment is as shown in the following Scheme (4):

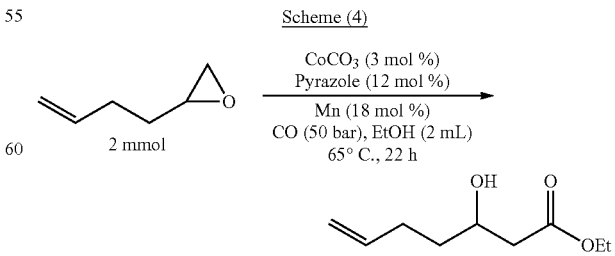

Scheme (4)

The specific steps are as follows: 7.14 mg of CoCO$_3$ and 19.78 mg of manganese powder are placed in the reactor; the reactor is filled with nitrogen and then evacuated, and thus repeated three times to obtain a nitrogen atmosphere, and 2 mL of ethanol is added to the reactor, and 196.3 mg (2 mmol) of 2-(3-butenyl)oxirane and 16.34 mg of pyrazole, then replacing the nitrogen in the reactor with carbon monoxide gas, replacing it three times, then charging carbon monoxide to 5 MPa, raising the temperature to 65° C., and reacting for 22 hours. After the reaction is completed, the obtained reaction liquid is subjected to distillation under reduced pressure to give 295 mg of a colorless transparent liquid, having a content of 99% and a yield of 85%.

Figure 9:
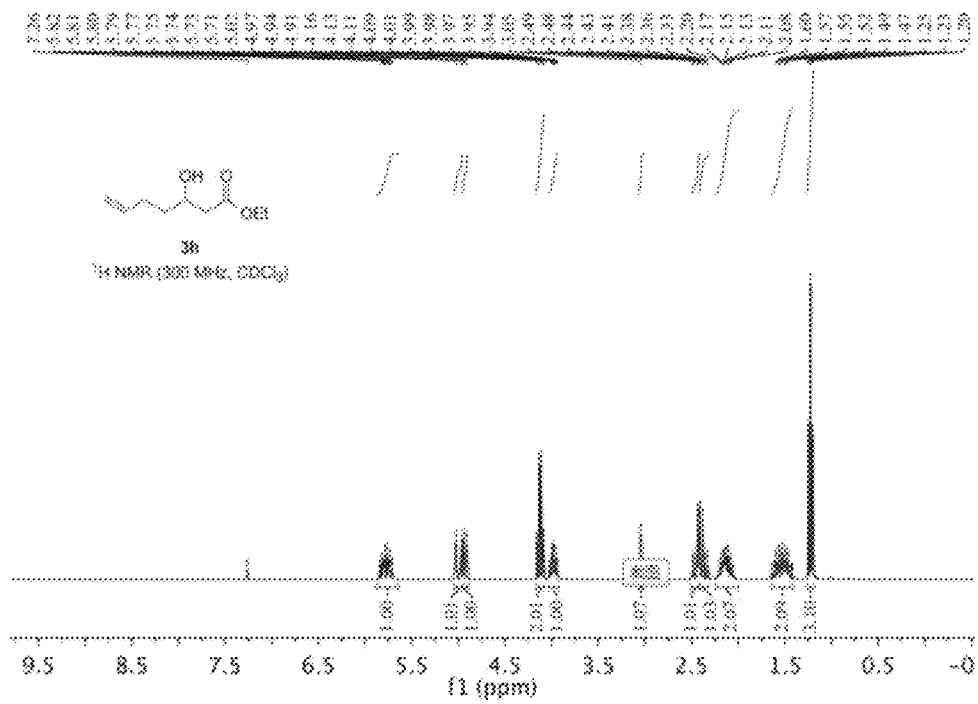
FIG. 9 is the hydrogen spectrum of the product obtained in Example 4.
Figure 10:
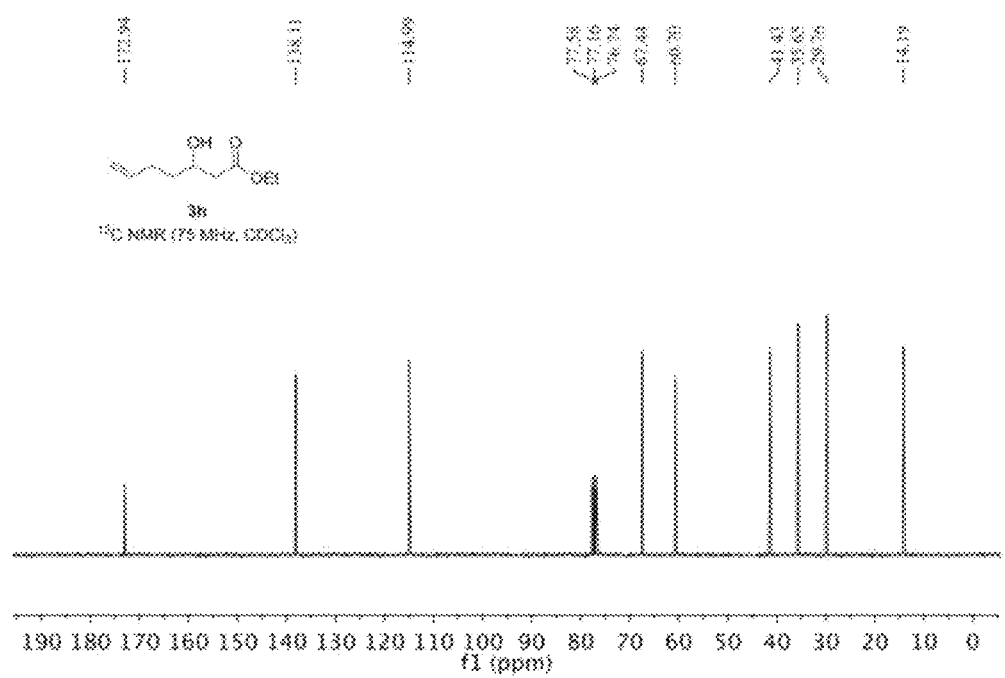
FIG. 10 is the carbon spectrum of the product obtained in Example 4.

The product obtained in this example is characterized by NMR, and the analytical maps are shown in FIGS. 9 and 10, and the results are as follows:

$^1$H NMR (300 MHz, CDCl$_3$) δ 5.91-5.65 (m, 1H), 5.00 (d, J=17.1 Hz, 1H), 4.93 (d, J=10.2 Hz, 1H), 4.12 (q, J=7.1 Hz, 2H), 4.03-3.93 (m, 1H), 3.05 (s, 1H), 2.46 (dd, J=16.3, 3.7 Hz, 1H), 2.37 (dd, J=16.3, 8.5 Hz, 1H), 2.25-1.98 (m, 2H), 1.75-1.38 (m, 2H), 1.23 (t, J=7.1 Hz, 3H).

$^{13}$C NMR (75 MHz, CDCl$_3$) δ 172.94, 138.11, 114.99, 67.44, 60.70, 41.43, 35.65, 29.76, 14.19.

The product obtained in this example is analyzed by gas chromatography-mass spectrometry and the results are as follows:

GC-MS (EI, 70 eV): m/z (%)=171(1), 154(25), 143(8), 130(33), 117(100), 109(40), 81(100), 71(99).

According to the above analysis, the product obtained in the present application is ethyl 3-hydroxy-6-alkenylheptanoate having the structure of the product shown in the scheme (4).

The invention is not limited by the embodiments described above which are presented as examples only but can be modified in various ways within the scope of protection defined by the appended patent claims.

What is claimed is:

1. A method for preparing a β-hydroxycarboxylic acid ester, comprising the steps of:
    mixing an alkylene oxide, a monohydric alcohol, and a composite catalyst, and
    performing a carbonylation esterification reaction in a carbon monoxide atmosphere to obtain the β-hydroxycarboxylic acid ester;
    wherein the composite catalyst comprises a main catalyst, a cocatalyst, and a reducing agent;
    the main catalyst comprises at least one of a cobalt salt and a cobalt hydroxide;
    the cocatalyst is a nitrogen-containing heterocyclic compound; and
    the reducing agent is a base metal wherein the cobalt salt is selected from the group consisting of cobalt fluoride, cobalt chloride, cobalt bromide, cobalt iodide, cobalt acetate, cobalt carbonate, cobalt nitrate, cobalt sulfate, and combinations thereof;
    wherein the nitrogen-containing heterocyclic compound is selected from the group consisting of a pyrazole compound, an imidazole compound, a pyridine compound, and a quinolone compound;
    and wherein the base metal is selected from the group consisting of iron, zinc, manganese, nickel copper, and aluminum.

2. The method according to claim 1, wherein the ratio of the molar amounts of the main catalyst, the cocatalyst, and the reducing agent is 1:(2 to 6):(2 to 10).

3. The method according to claim 1, wherein the amount of the main catalyst is from 0.5 to 5 mol % based on the alkylene oxide.

4. The method according to claim 1, wherein the pyrazole compound is selected from the group consisting of pyrazole, 1-methylpyrazole, and 2-methylpyrazole; and the imidazole compound comprises at least one of imidazole, 1-methyl imidazole, 4-phenylimidazole, and 1-acetylimidazole; the pyridine compound comprises at least one of pyridine, 3-hydroxypyridine, 2-hydroxypyridine, 2-aminopyridine, 4-aminopyridine, 4-N,N-dimethyl Pyridine, 2,2-bipyridine, and 4,4-bipyridine; the quinoline compound comprises at least one of quinoline, isoquinoline, and 8-hydroxyquinoline.

5. The method according to claim 1, wherein the ratio of the alkylene oxide to the monohydric alcohol is 1 mmol:1 to 5 mL.

6. The method according to claim 1, wherein the carbonylation esterification reaction is carried out at a pressure of 3 to 10 MPa, a temperature of 40 to 120° C., and a time of 10 to 30 hours.

* * * * *